US00PP11642P

United States Patent [19]

Noodelijk

[11] Patent Number: Plant 11,642

[45] Date of Patent: Nov. 21, 2000

[54] CHRYSANTHEMUM PLANT NAMED 'REMCO'

[75] Inventor: Robert Noodelijk, Woubrugge, Netherlands

[73] Assignee: Chrysanthemum Breeders Association N.V., Netherlands

[21] Appl. No.: 09/149,459

[22] Filed: Sep. 9, 1998

[51] Int. Cl.[7] ..... A01H 5/00

[52] U.S. Cl. ..... Plt./286

[58] Field of Search ..... Plt./286, 287, 297, Plt./294

[56] References Cited

U.S. PATENT DOCUMENTS

P.P. 6,621 2/1989 Mack et al. ..... Plt./289

*Primary Examiner*—Howard J. Locker
*Attorney, Agent, or Firm*—Parkhurst & Wendel, L.L.P.

[57] ABSTRACT

A new and distinct cultivar of chrysanthemum plant named Remco, bearing medium sized blooms with pinkish white ray florets and an orange-red center and performance of 21 days.

2 Drawing Sheets

BACKGROUND OF THE INVENTION

The new plant of the present invention comprises a new and distinct cultivar of chrysanthemum plant that was discovered and selected as one flowering plant within the progeny of a cross of a pollination of a group of chrysanthemum cultivars on a female parent chrysanthemum cultivar named 'Dark Eyes' (U.S. Plant Pat. No. 8,244) in a controlled environment in Ter Ar, Holland.

The first act of asexual reproduction of Remco was accomplished when vegetative cuttings were taken from the initial selection in August 1992 in a controlled environment in Ter Ar, Holland.

SUMMARY OF THE INVENTION

The present invention is a new and distinct variety of chrysanthemum bearing medium sized blooms with pinkish-white ray florets and a orange-red center.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
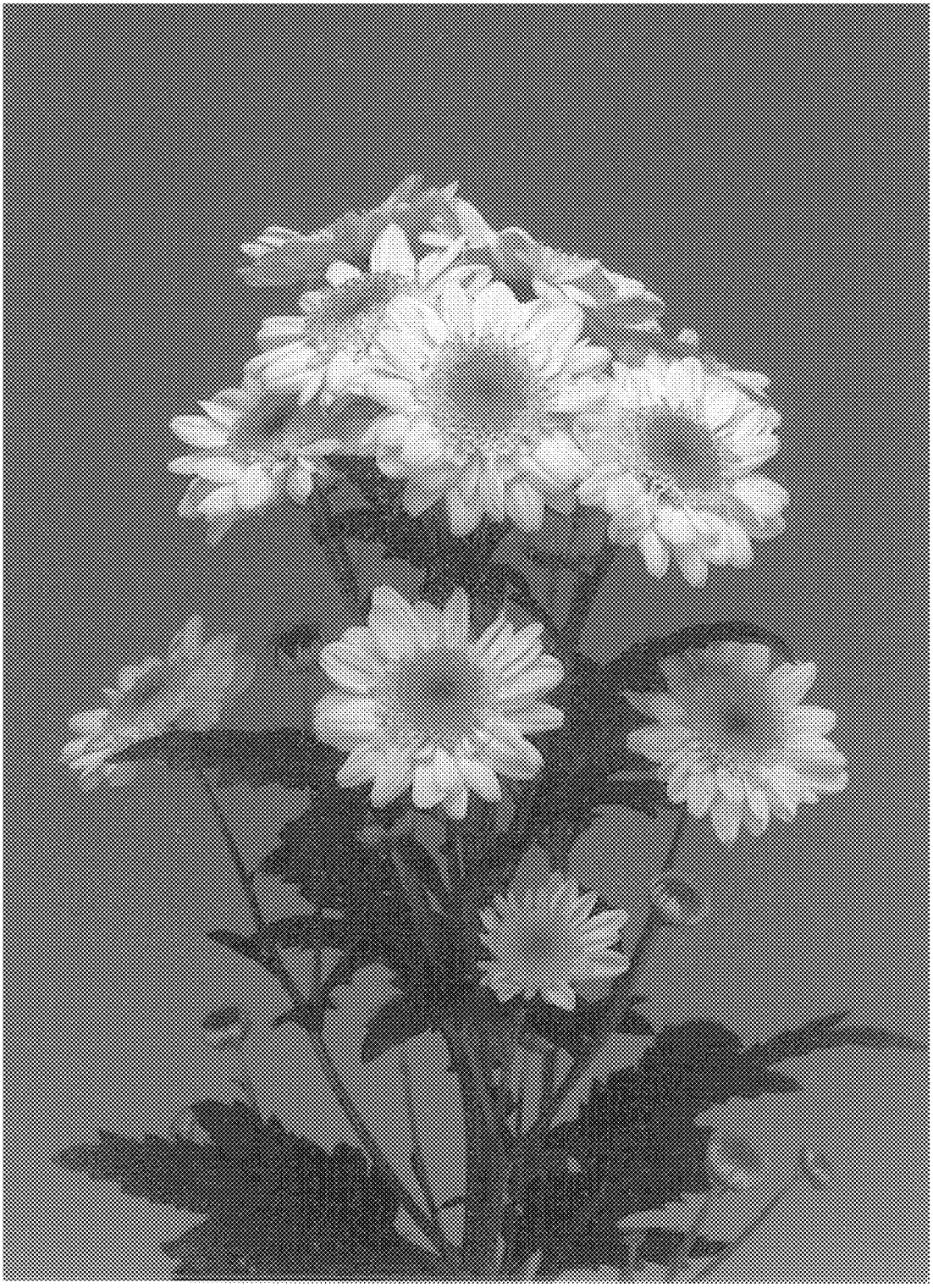
FIG. 1 shows the stem of the cultivar in full bloom.
Figure 2:
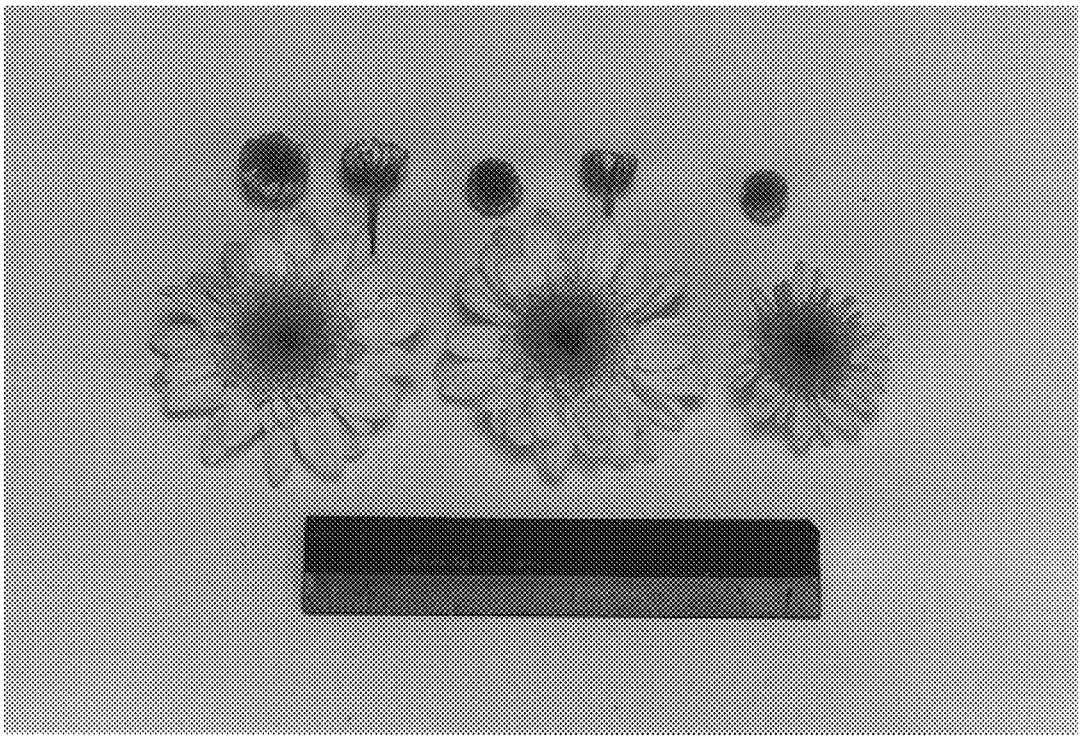
FIG. 2 shows the various stages of bloom of the new cultivar.
Figure 3:
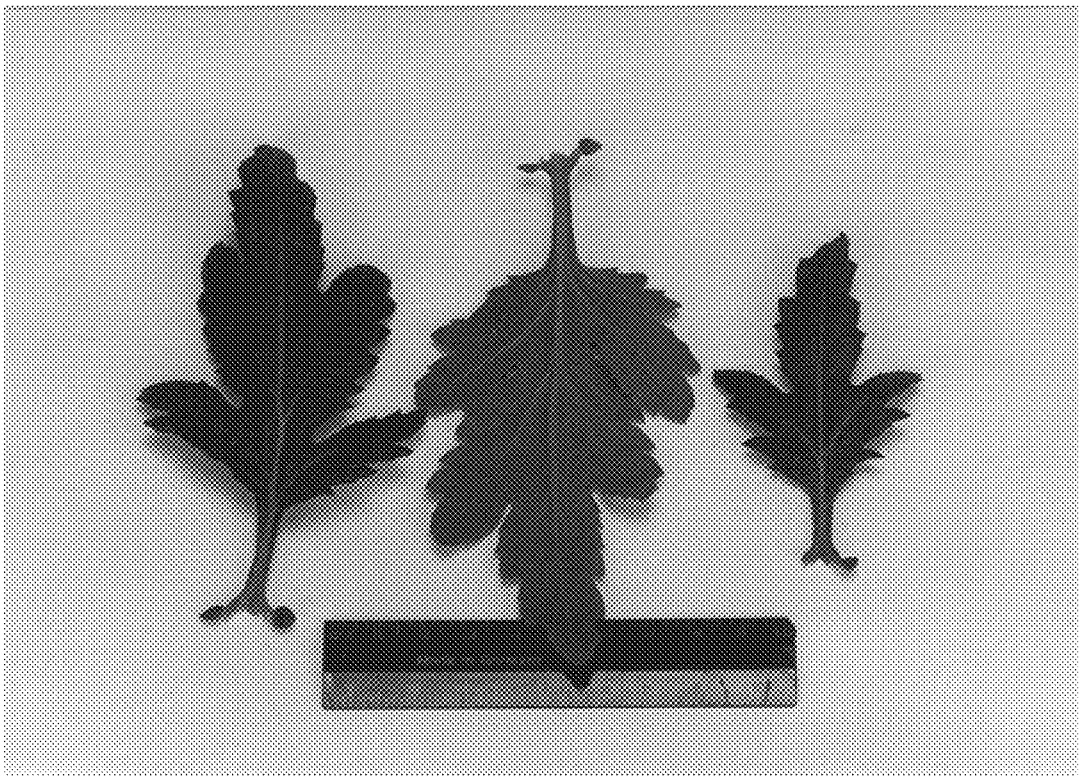
FIG. 3 shows foliage and petiole of the new cultivar.

This new variety of chrysanthemum is of the botanical classification *Dendranthema grandiflora*. When grown in the vicinity of Ter Aar, Holland, it has a response time of approximately 8 weeks. This new variety produces medium sized blooms with pinkish-white ray florets and an orange-red center having a 3 week performance (i.e., vase life of 21 days). This new variety of chrysanthemum has been found to retain its distinctive characteristics throughout successive propagations. However, the phenotype may vary significantly with variations in environment such as light intensity and temperature. To show the phenotype as described, Remco may be planted under greenhouse conditions in Holland without assimilation lightning between week 2 and 40. With assimilation lightning (minimum level 2500 lux), Remco may be planted yearround under greenhouse conditions in Holland.

The following is a description of the plant and characteristics (color designations are from The R.H.S Colour Chart) that distinguish it from related known varieties and its antecedents. In the following table format, botanical information is also set forth for 'Remco Yellow', a related cultivar which is described in U.S. Plant patent application Ser. No. 09/149,461.

The color designations are taken from the plant itself. Accordingly, any discrepancies between the color designations and the colors depicted in the photographs are due to photographic tolerances.

Botanical Description of Remco and Remco Yellow

| CULTIVAR | REMCO | REMCO YELLOW |
|---|---|---|
| Bud | | |
| Size | large cross section ± 1.5 cm height ± 1.2 cm | large cross section ± 1.5 cm height ± 1.2 cm |
| Outside Color | Mainly red 49D, red-purple 64D at the tip | yellow-orange 21A to red 46A at the tip |
| Bloom | | |
| Size | medium | medium |
| Fully Expanded | 6–6½ cm | 6–6½ cm |
| Borne | upper portion single flower per peduncle, lower portion plural flower per penduncle | upper portion single flower per peduncle, lower portion plural flower per penduncle |
| Number of Blooms per single stem | average of 11 | average of 11 |
| Peduncle Lengths | Near the top ±12 cm, near the middle ±26 cm, near the bottom ±28 mm. | Near the top ±12 cm, near the middle ±26 cm, near the bottom ±28 cm. |
| Peduncle Lateral Shoot, Attachment | medium | weak to medium |
| Peduncle Lateral Shoot, Angle | 40° | 35°–30° |
| Form | semi-double (anemone) | semi-double (anemone) |
| Performance | Good, 21 days (18°–20° C.) | Good, 21 days (18°–20° C.) |

-continued

Botanical Description of Remco and Remco Yellow

| CULTIVAR | REMCO | REMCO YELLOW |
|---|---|---|
| Color | | |
| Center of Flower/ Disk floret | Between orange-red 33B and 34A with a dot in very center of red 53B | Greyed-orange 170A with a dot in the very center of greyed-red 178C |
| Color of the upper surface of the majority of the ray-florets | Red-purple 69C but slightly more white | Yellow-orange 16A |
| Color of the lower surface of the majority of the ray-florets. | red-purple 69B but slightly paler | yellow 10C with greyed-red 182D between the ribs |
| Tonality from Distance | a pinkish white anemone type flower with orange-red cushion | a yellow anemone type flower with a red teint and a greyed-orange cushion |
| Discoloration | ray-florets to almost white, center (cushion) to orange-red 34C | ray-florets to yellow-orange 16C, cushion to yellow 13A with greyed-red 178A at the tips |
| Pollen | not present | not present |
| Ray Florets | | |
| Texture | upper side smooth, under side smooth | upper side smooth, under side smooth |
| Number | 25–30 (two rows) | 25–30 (two rows) |
| Cross-section | convex, no keels | convex, two keels |
| Longitudinal axis of majority | reflexing | straight |
| Shape of tip | dentate | rounded |
| Fragrance | typical chrysanthemum | typical chrysanthemum |
| Disc Diameter | large to very large (2.5–3.0 cm) | large to very large (2.5–3.0 cm) |
| Reproductive Organs | | |
| Stamen (present in disc florets only) | yellow-green, thick ± 5 mm in length | yellow-green, thick ± 5 mm in length |
| Pollen | not present | not present |
| Styles (present in disc and ray florets) | green, thick | green, thick |
| Style Length | ±7 mm | ±7 mm |
| Stigmas | yellow-green | yellow-green |
| Stigma Width | ±3 mm | ±3 mm |
| Ovaries | enclosed in calyx | enclosed in calyx |

-continued

Botanical Description of Remco and Remco Yellow

| CULTIVAR | REMCO | REMCO YELLOW |
|---|---|---|
| Plant | | |
| Form | spray mum meant for erect culture-Herbaceous | spray mum meant for erect culture-Herbaceous |
| Growth | medium | medium |
| Height | ±110–120 cm | ±110–120 cm |
| Stem Color | green 139A | green 146A |
| Stem Strength | medium to strong | medium to strong |
| Stem Brittleness | absent | present |
| Stem Anthocyanin Coloration | present (mainly at the base) | present (mainly at the base) |
| Internodes | medium (2.5–3.0 cm) | medium (2.5–3.0 cm) |
| Flowering Response (photoperiodic controlled crop, no natural growing) | 8 weeks | 8 weeks |
| Foliage | | |
| Color | upper side between 137A and yellow-green 147A, underside near green 137B | upper side between 137A and yellow-green 147A, underside near green 137B |
| Size | length ±12 cm, width ±6 cm | length ±12 cm, width ±6 cm |
| Quantity (per single stem) | 22–26 | 22–26 |
| Shape | lobed | lobed |
| Texture | fleshy | fleshy |
| Ribs and Veins | ribs well developed, veins not so developed | ribs well developed, veins not so developed |
| Edge | crenated | crenated |
| Shape of Base of Sinus Between Lateral Lobes | round | round |
| Margin of Sinus Between Lateral Lobes | converging | converging |
| Shape of Base | uneven | uneven |
| Apex | cuspidate | cuspidate |
| Year of Discovery | 1992 | 1993 |

I claim:

1. A new and distinct variety of chrysanthemum plant as described and illustrated.

* * * * *